United States Patent [19]

Baum et al.

[11] 4,291,577

[45] Sep. 29, 1981

[54] ON LINE ULTRASONIC VELOCITY GAUGE

[75] Inventors: Gary A. Baum; Charles C. Habeger, both of Appleton, Wis.

[73] Assignee: The Institute of Paper Chemistry, Appleton, Wis.

[21] Appl. No.: 99,410

[22] Filed: Dec. 3, 1979

[51] Int. Cl.³ ............................................. G01N 29/00
[52] U.S. Cl. ........................................ 73/597; 73/639; 73/159; 310/334
[58] Field of Search ............... 73/597, 574, 618, 624, 73/625, 628, 639, 641, 159, 32 A; 310/334, 336

[56] References Cited

U.S. PATENT DOCUMENTS

| | | | |
|---|---|---|---|
| 2,625,035 | 1/1953 | Firestone | 310/336 |
| 3,850,031 | 11/1974 | Schwenzfeier et al. | 73/159 |
| 4,202,216 | 5/1980 | Bull et al. | 73/639 |

FOREIGN PATENT DOCUMENTS

| | | | |
|---|---|---|---|
| 938125 | 12/1973 | Canada . | |
| 489036 | 10/1975 | U.S.S.R. | 73/597 |
| 601609 | 4/1978 | U.S.S.R. | 73/597 |

OTHER PUBLICATIONS

E. P. Papadakis, "Ultrasonic Methods for Modulus Measurement in Paper", *Tappi*, vol. 56, No. 2, pp. 74-77, Feb. 1973.

M. T. Lu, "On Line Measurement of Strength Characteristics of a Moving Sheet", *Tappi*, vol. 58, No. 6, pp. 80-81, Jun. 1975.

*Primary Examiner*—Stephen A. Kreitman
*Attorney, Agent, or Firm*—Fitch, Even, Tabin, Flannery & Welsh

[57] ABSTRACT

A device which measures the velocity of ultrasonic waves in a moving web is provided. A pair of wheels is mounted for continuous surface contact with the paper and a transducer, which contacts the web on each revolution, is located in each wheel for relating electrical and mechanical signals. Timing means measures the time it takes a mechanical signal generated at the first wheel to reach the second wheel. Noise reducing and amplifying means are provided for effective operation.

21 Claims, 9 Drawing Figures

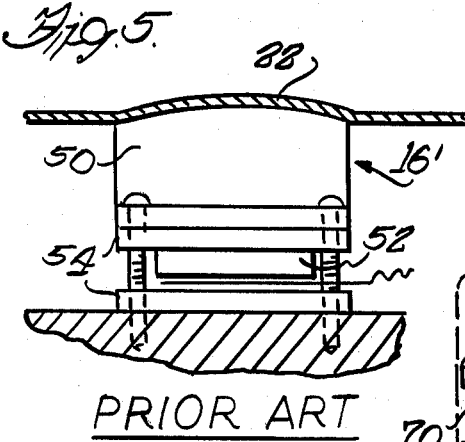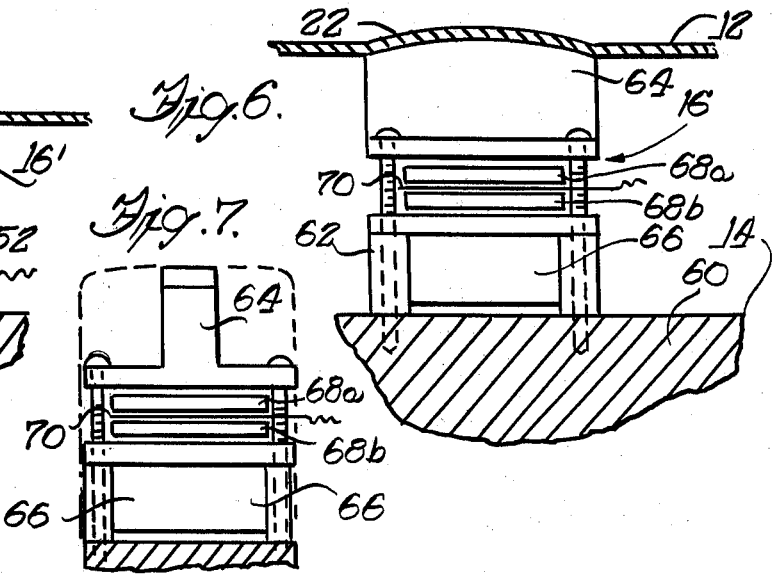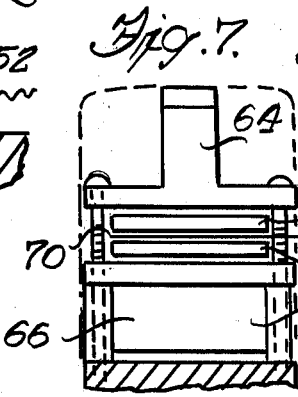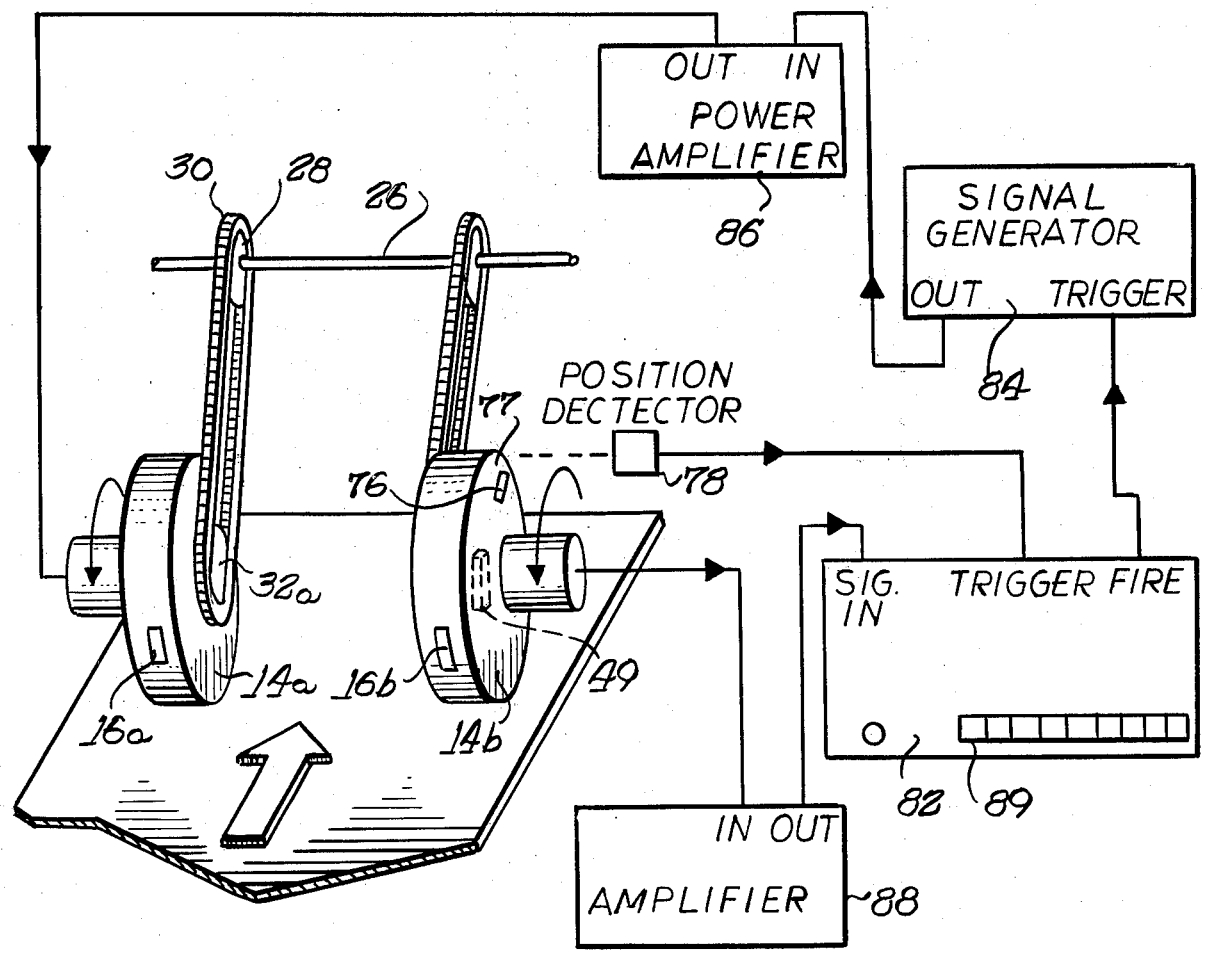

ON LINE ULTRASONIC VELOCITY GAUGE

The present invention relates to gauges for continuously measuring paper mechanical properties and paper strength, and more particularily, to a gauge to determine paper mechanical properties and strength by measurements of ultrasonic waves through paper. It applies to other webs as well.

Nearly all end use applications of paper or paperboard have certain required strength specifications. Strength parameters have been established to describe burst strength, tensile strength, pierce strength, edge strength, hold strength, etc. The strength parameters of paper are ordinarily determined by various destructive tests. Samples of mill-produced paper are subjected to various forms of stress until the paper breaks or tears.

Relying for paper strength only on the destructive tests has several disadvantages. Strength parameters determined by destructive tests may only be measured after the paper is produced. Thus, if it is found that a substantial amount of paper has been produced which does not measure up to the required specifications, a large quantity of paper could be wasted. Furthermore, a destructive test for paper is only truly valid for the particular sample of paper tested. It does not measure uniformity and it may not be representative. Of course, the more samples taken from paper the more representative the testing will be. However, when one is producing, for example, a large roll of paper it is not desirable to cut pieces out of the middle. Therefore, samples may only be taken, as a practical matter, where the paper is cut, i.e. between rolls. Even multiple sampling does not insure that non-uniform areas of the paper do not have weaknesses, and in certain applications a weak section of paper could have very adverse consequences.

It is therefore desirable to test paper for various strength parameters on line. However, this is not feasible to do directly. Paper from a mill is produced in a continuous fast moving web.

It has been known that many of the strength parameters of paper are related to Young's modulus of elasticity. Thus, if an estimate of Young's modulus of elasticity could be obtained continuously, general estimates of strength of a moving web of paper are possible. Furthermore, continual monitoring of the Young's modulus would be an indication of uniformity of the paper web. As with other parameters of paper, it is not possible to continuously measure Young's modulus directly. However, it has been discovered that there is a correlation between Young's modulus and the velocity of sound waves through paper.

Therefore, if one can continually monitor the velocity of ultrasound waves through a moving paper web, one will be able to estimate Young's modulus of elasticity and, hence, the strength and uniformity of the paper web.

While wave propagation through paper is complex, in a simplified model the velocity U of ultrasound waves through paper is related to Young's modulus E by the formula $U^2 = E/\rho(1 - V(xy) \cdot V(yx))$ where $V(xy)$ and $V(yx)$ are the in-plane Poisson's ratios and $\rho$ is the density of the paper. Since the term $(1 - V(xy) \cdot V(yx))$ is typically near unity having values between 0.9 and 1.0, E can be estimated from $U^2$. If U, can be measured, it would be possible to get an estimation of the Young's modulus of elasticity. In an on-machine situation it would not be desirable to have to measure the apparent density, $\rho$. If $U^2$ is multiplied by the basis weight, a parameter already measured routinely on-machine, however, the result is an extensional stiffness, S (modulus times caliper). This is the parameter which correlates with tensile strength. Thus if one can measure both basis weight and sound velocities in the machine direction (MD) and cross-machine direction (CD), the following quantities are obtained:

(1) $U_{MD2}$ and $U_{CD2}$, measures of the stiffness per unit mass in the MD and CD, respectively;

(2) $S_{MD}$ and $S_{CD}$, extensional stiffnesses in the MD and CD directions, respectively, which correlate with tensile strengths in these directions; and, (3) $S_{MD}/S_{CD}$, a measure of the "squareness" or anisotropy in the sheet. Note from equations one and two that the ratio does not involve the approximation involving Poisson ratios noted earlier. Also, the anisotropy ratio R has been shown to correlate very well with similar ratios determined from stress-strain curves.

Stiffness values are quite sensitive to changes in refining, pressing, and drying conditions, and the measure of stiffness might be used to monitor one of these during the sheetmaking process. Elastic moduli, of course, are also quite sensitive to moisture content, and it would be necessary to have a simultaneous measure of moisture in order to correct the results for this effect. The anisotropy ratio, sensitive to fiber orientation and drying restraints, is quite insensitive to changing moisture.

The stiffnesses and anisotropy ratio may be used as measures of product quality while the sheet is being manufactured. A device which can measure these parameters, therefore, could be used as a process control sensor or as a continous indicator of product quality.

Various factors complicate the measurement of ultrasound velocity through paper. The machinery which produces paper also produces various mechanical noise including ultrasound waves. Therefore, any transmittal of ultrasound waves through paper must be strong enough to overcome the background noise and any receiver of ultrasonic waves must be quite sensitive. Any signal from the receiver will be quite weak and must be amplified. Furthermore, any mechanical measuring device will itself create a certain amount of mechanical noise which causes problems.

It is a principal object of the present invention to produce means which will reliably measure the velocity of ultrasonic waves through paper.

SUMMARY OF THE INVENTION

The invention provides a device having two spaced wheels which roll along the moving paper web. The first wheel contains a transmitting transducer. When the transducer contacts the paper, on each revolution of the wheel, it receives an electrical signal from a signal generator, and imparts a mechanical signal to the paper. The second wheel contains a receiving transducer which also contacts the paper once each revolution and receives the signal from the transmitter by picking up the ultrasound signal from the paper and converts it to an electrical signal. The signal is transmitted to a metering and recording apparatus which measures the velocity of the ultrasonic waves. In order that the signal to noise ratio be sufficiently great, the gauge includes appropriate noise reducing means and signal amplifying means.

FIG. 4 is a diagramatic view of the ultrasound velocity gauge connected to the electronic measuring equipment.

FIG. 5 is a side elevation view of a prior art transducer used in the measurement of paper hardness.

FIG. 6 is a side elevation view of a transducer modified for use in the ultrasound velocity gauge.

FIG. 7 is a front elevation view of the transducer illustrated in FIG. 6.

Figure 1:
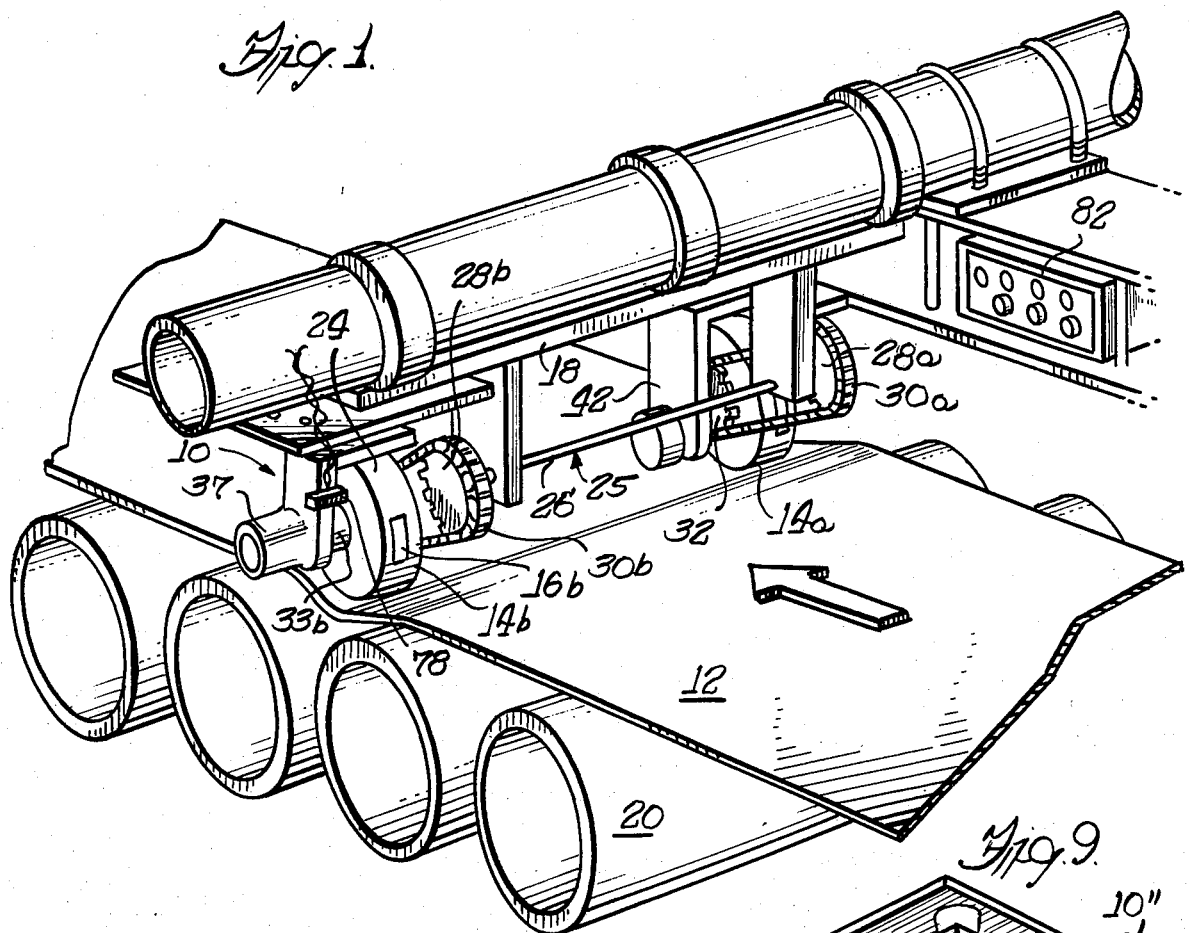
FIG. 1 is a perspective view of an ultrasound velocity gauge shown on a moving web of paper.

In FIG. 1 is shown a gauge 10 to measure ultrasound velocity. A pair of transversely spaced wheels 14a and 14b roll along and maintain surface contact with a moving web of paper 12 and serve to transmit ultrasonic waves transversely of the web 12. The first wheel 14a contains a first transducer 16a which imparts an ultrasonic signal to the web 12. The second wheel 14b contains a second transducer 16b which touches the web 12 at an appropriate time to pick up the signal wave generated by the first transducer 16a and converts it to an electrical signal which is transmitted to an electronic metering apparatus which measures the time it takes the ultrasonic signal to travel from the first wheel 14a to the second wheel 14b.

SPECIFIC EXAMPLE

So that the invention may be fully understood, the invention will now be described in greater detail.

The wheels 14a and 14b employed in this invention are known to those skilled in the art. A modification of the type of wheels sold by Consolidated Bathurst to test for paper hardness is preferrably used in the gauge of the present invention. The wheels 14a and 14b, therefore, will not be described in greater detail than is necessary to describe the invention and only those modifications will be described in detail which adapt prior art wheels for use in the ultrasound velocity gauge 10. Like the prior art wheels, the wheels 14 used in the present invention have mounted therein piezoelectric transducers 16, and ultrasonic signals are transmitted between the wheels 14a and 14b. Mercury slip rings are on the wheels to provide electrical contact to external means.

Figure 2:
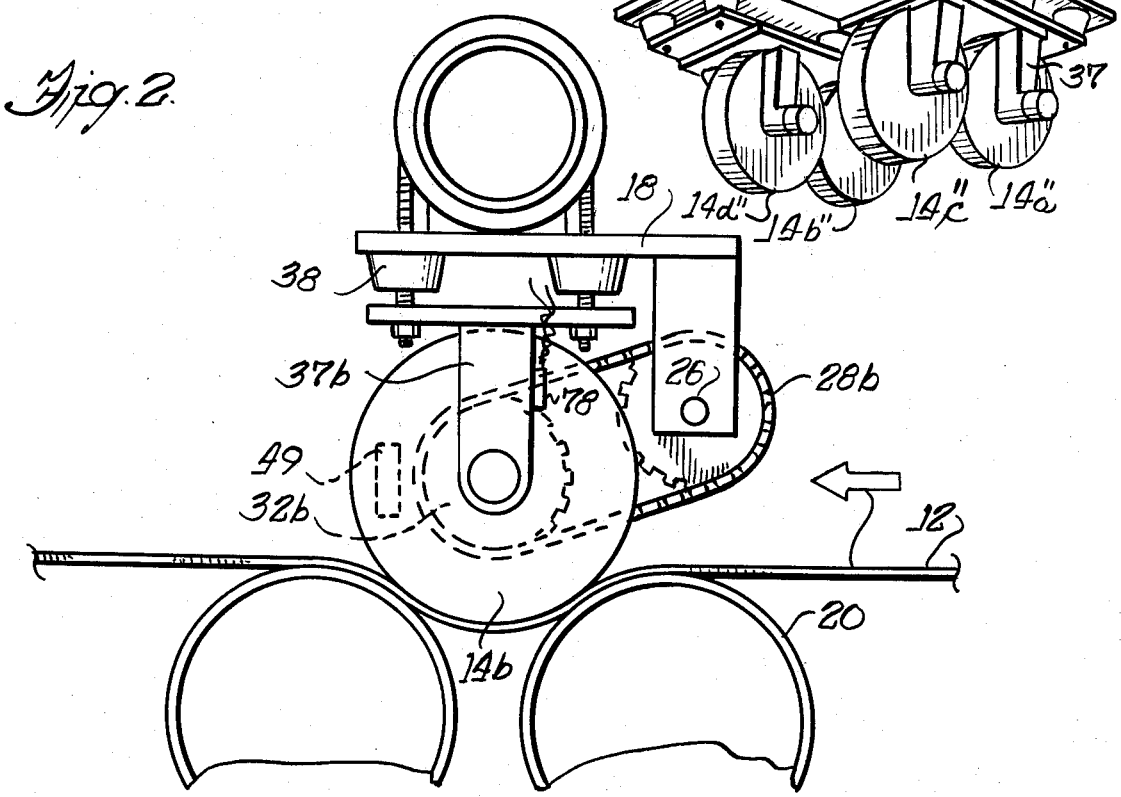
FIG. 2 is a side elevation view of the velocity gauge shown in FIG. 1.
Figure 3:
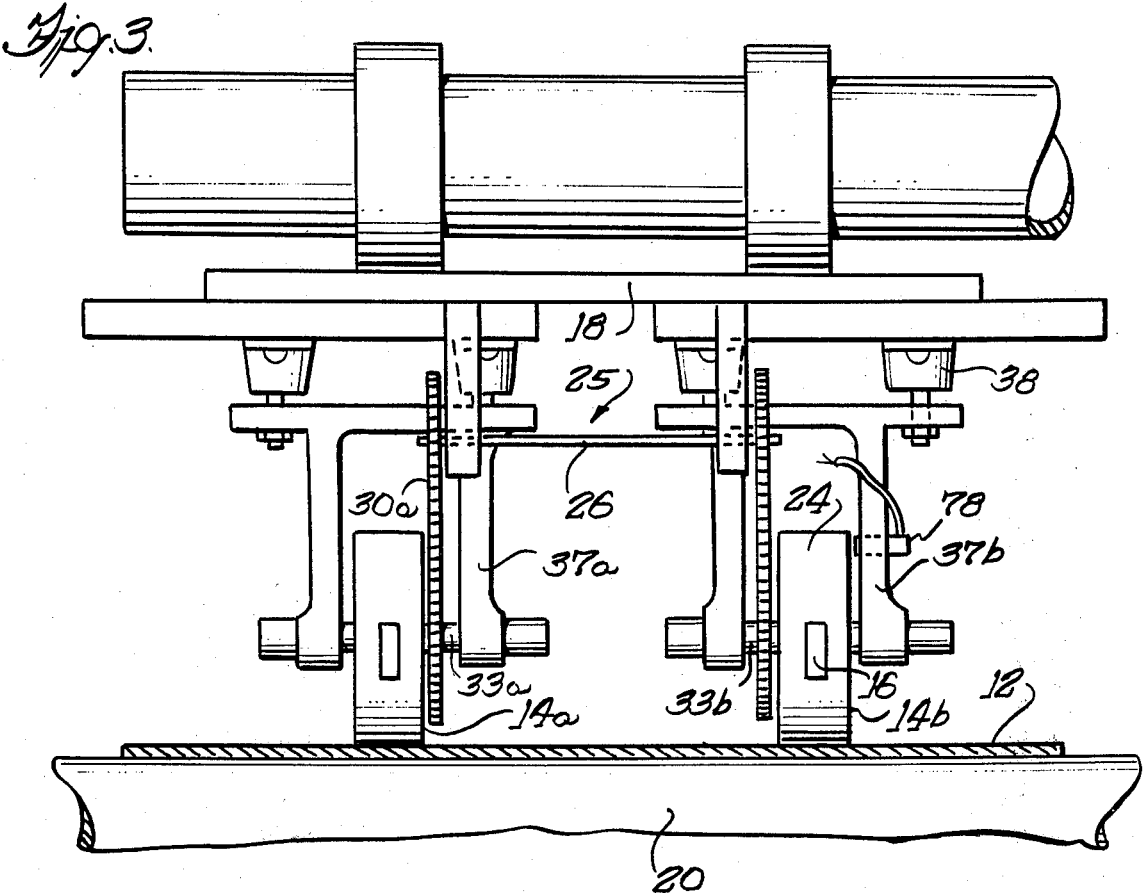
FIG. 3 is a front elevation view of velocity gauge shown in FIG. 1.

The first or transmitting wheel 14a and the second or receiving wheel 14b are supported from a platform 18 positioned above the moving paper web 12. The web is carried on a support means which may include, to facilitate movement of the web, a plurality of rollers. The wheels 14a and 14b may be positioned so that the web 12 passes between two longitudinally spaced rollers 20 and the wheels 14a and 14b of the gauge 10, as particularly seen in FIG. 2.

The first transducer 16a and second transducer 16b are mounted in the wheels 14a and 14b to effect contact with the web surface. Each transducer 16a and 16b has a surface which is generally continuous with the peripheral surface 24 of each wheel 14a and 14b, but the transducer surface may protrude slightly from the peripheral surface 24 of the wheels 14a and 14b to insure a good contact between the transducers 16a and 16b and the web 12.

In order that the receiving transducer 16b receives the signal, it is necessary that the receiving transducer 16b be on the web 12 at a time that it can receive the signal from the transmitting transducer 16a. Accordingly, the rotation of the first wheel 14a and the second wheel 14b are synchronized by a timing rod-chain mechanism 25. The timing rod mechanism comprises a timing rod 26, and mounted at each end is a coaxial sprocketed wheel 28a and 28b. A chain 30a and 30b from each sprocketed wheel 28a and 28b links each wheel on the rod 26 to a cooperating sprocketed wheel 32a and 32b which is keyed to an axle 33a and 33b which carries the wheels 14a and 14b containing the transducers 16a and 16b.

A major difficulty in constructing an ultrasonic velocity gauge 10 to measure the velocity of sound waves through a moving paper web 12 is obtaining sufficiently large signal to noise ratios. Contributing to the low signal to noise ratio is the poor sound conductance of the web 12. The signal received by the second or receiving transducer 16b is faint relative to the signal generated by the first or transmitting transducer 16a. The paper machine on which the web 12 is conveyed contains rotating and vibrating parts which also send noise to the second transducer 16b. Furthermore, the wheels 14a and 14b rolling on the paper 12 result in vibration. Electronic noise is created in the mercury slip rings which transmit the electrical signals to and from the rotating wheels 14a and 14b, and the noise is transmitted to the external apparatus. Accordingly, the components of the gauge 10 are designed and arranged to minimize extraneous noise and to enhance the signal relative to the noise so that the external apparatus may effectively measure the signal.

In order to minimize signal loss through the web 12, the wheels 14a and 14b are spaced relatively close together, i.e. about 20 cm. The spacing between the wheels is not very critical, however, to achieve the results of the invention. Sound velocities and transmission times of ultrasonic waves through the paper vary slightly, and precise means are required to measure the velocity.

In order to reduce extraneous noise, each wheel 14a and 14b is separately shock mounted on support means 37a and 37b. Supports 37a and 37b, which carry the axles 33a and 33b, are suspended from the platform 18 by shock absorbers 38 of resilient sound absorbing material.

Because electronic noise is generated by the mercury slip rings, a preamplifier 49 is mounted in the second wheel 14b to amplify the signal from the second transducer 16b prior to transmission through the slip rings.

The transducers 16a and 16b of the present invention are an improvement over the prior art transducers 16' shown in FIG. 5, and provided in the prior art wheel. In the prior art, an aluminum button 50 is mounted in the wheel 14 to contact the web 12 and transmit a signal to a piezoelectric crystal 52 which is sandwiched between two PC boards 54. The prior art transducer 16' proved unsuitable for an ultrasonic velocity gauge 10 since the signal thereby produced was too weak. Accordingly, improved transducers 16a and 16b, as shown in FIGS. 6 and 7, were designed for use in the ultrasonic velocity gauge 10 of the invention.

The transducers 16 used in the present invention are mounted above the base 60 of the wheels 14 on sound absorbing standoffs 62, preferably made of polymerized tetrafluoro ethylene such as that sold under the trademark Teflon, to reduce noise from the wheel 14. An aluminum button 64 distal to the wheel base 60 and an aluminum ballast 66 proximal to the wheel base 60 are mounted on the standoffs 62 and have sandwiched therebetween a pair of piezoelectric crystals 68a and 68b preferably made of lead zirconate titanate. An electrode 70 is positioned between the crystals 68.

The first crystal 68a is in surface contact with the aluminum button 64 for transmission of ultrasonic vibrations. The second crystal 68b is selected for in phase oscillation with the first crystal 68a for signal amplification. The aluminum ballast 66 in surface contact with the second crystal 68b reduces surface reflection in the second crystal 68b. The crystals 68 are in surface contact with the electrode 70 for electrical transmission therebetween.

Illustrated in FIG. 4 is a schematic diagram of the ultrasonic velocity gauge 10 and the external metering apparatus. The electronic equipment is comprised of available items known in the art and accordingly will be described in no greater detail than is necessary to discuss their relationship to the ultrasonic velocity gauge 10.

In order that the velocity of the sound waves through the web 12 can be gauged, it is necessary that a short signal, preferably a burst of sine waves, be supplied to the web 12 when the first transducer 16a is in contact with the web 12. As mentioned above, the rotation of the first wheel 14a and the second wheel 14b are synchronized as a consequence of the timing chain mechanism 25. An indicator 76 having a surface with different light reflective properties than the side surface 77 of the second wheel 14b is positioned on the side surface 77 of the second wheel 14b so that it may be detected by a light beam position detector 78. The indicator 76 may be in the form of a non-reflective surface which contrasts with a shiny side surface 77 of the wheel 14b and is positioned to be in front of the light beam position detector 78 when the transmitting transducer 16a is on the web 12.

The position of the indicator 76 on the side 77 of the second wheel 14b is a convenient location, but other locations for the indicator 76 are appropriate. Various means of detecting position of the wheel 14b may be employed without departing from the scope of the invention. However, a light beam position detector 78 is particularly preferred because nothing touches the wheel 14 and consequently no extraneous noise is thereby introduced.

When the position detector 78 determines that the first transducer 16a is on the web 12, it transmits a signal to an external control unit 82. The control unit 82 activates a timing means contained therein and simultaneously activates a signal generator 84. The signal produced by the signal generator 84 is amplified by a power amplifier 86 which transmits the amplified signal to the first transducer 16a through the mercury slip rings.

The piezoelectric crystals 68 in the first transducer 16a convert the electrical signal to ultrasonic waves which are imparted to the web 12 by the aluminum button 64 of the first transducer 16a.

The ultrasonic waves propagate through the web 12 and are picked up by the aluminum button 64 of the second transducer 16b which is in contact with the paper 12 at a time to receive the signal. In practice, the two transducers 16a and 16b will contact the paper 12 generally simultaneously as the transmission time through about 20 cm of paper 12 is extremely short. Of course, the transmission time varies as the Young's modulus of elasticity of the paper 12 varies, but the contacting surface 22 of the aluminum button 64 of the receiving transducer 16b is long enough to contact the web 12 for a sufficient length of time so that it will be in contact with the paper 12 whenever the transmitted ultrasound signal reaches it.

The signal picked up by the aluminum button 64 of the second transducer 16b is converted to an electrical signal by the piezoelectric crystals 68 and transmitted to the electrode 70 sandwiched therebetween. The signal passes first to the preamplifier 49 mounted in the second wheel 14b and then through the mercury slip rings to an amplifier 88 to further amplify the signal. The amplified signal is transmitted to the timing means in the control box 82. The timing means in the control box 82 measures the time between the firing of the signal and the reception by the timing means of the electrical signal produced by the second transducer 16b.

The time measured by the timing means includes not only the time of transmission of the ultrasound waves, but the electrical transmission time in cables and electronics, and the transmission time of the ultrasound in the wheels 14. The ultrasound transmission time in the electronics and wheels 14 may be predetermined and subtracted from the measured time by computing means in the control box 82.

Computing means in the control box 82 may perform other computations to make the measured time more meaningful. For example, it is found that the average transmission times of a plurality of wheel revolutions, gives a more meaningful velocity reading than the velocity measured on a single revolution. The computing means accordingly may average the transmission time for a plurality of revolutions. The computing means may also calculate Young's modulus of elasticity from the measured velocities.

The control box 82 generates output signals to various readout devices. An output signal compatible with a digital readout 89 may be generated so that the ultrasonic velocities may be continuously monitored to alert an operator to any significant change in paper mechanical properties. An analog output from the control box 82 may be supplied to a recording chart (not shown) to provide a profile of the paper which has been monitored under the gauge.

Figure 8:
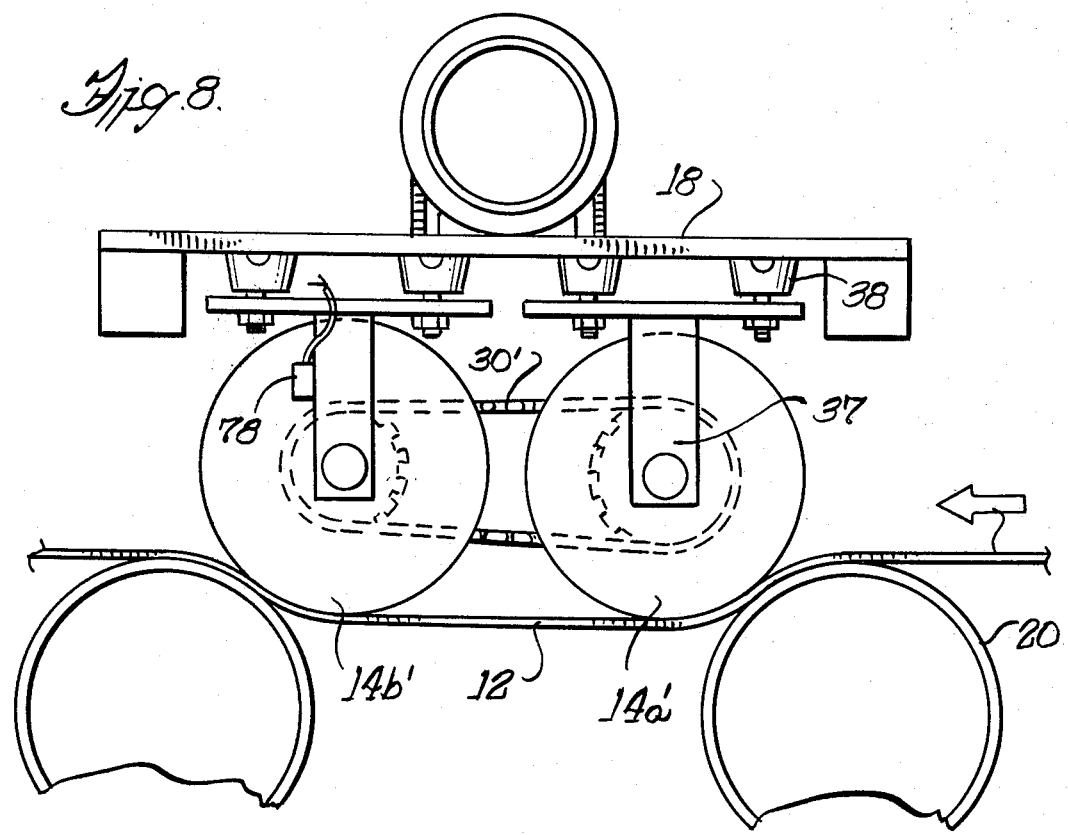
FIG. 8 is a side elevation view of an alternate embodiment of an ultrasound velocity gauge used to measure ultrasound velocities in the machine direction (direction of web travel).

As a result of factors inherent in paper manufacture, the Young's modulus in the machine direction usually differs from the Young's modulus in the cross machine direction. The ultrasonic velocity gauge 10, as illustrated in FIGS. 1–4 measures the cross machine velocity of sound waves through a moving web 12. Illustrated in FIG. 8 is a further embodiment of the invention in which an ultrasound velocity gauge 10' measures sound velocities in the machine direction. The machine direction velocity gauge 10' is substantially identical to the cross machine gauge 10 previously described except that the wheels 14' are longitudinally spaced from each other instead of being transversely spaced as described before.

The rotation of the wheels 14 in a machine direction velocity gauge 10' may be synchronized by a chain 30' directly connecting the sprocketed members 32' of the wheels 14.

While the movement of the web 12 might be expected to affect the ultrasonic velocity measurements, especially in the machine direction, the velocity of the web 12 may be considered negligible compared to the ultrasound velocities. Typical ultrasound velocities in paper are $2 \times 10^3$ m/sec to $4 \times 10^3$ m/sec, while typical machine web speeds are 10 to 30 m/sec.

Figure 9:
FIG. 9 is a perspective view of a further alternative embodiment of the present invention which measures ultrasound velocities both in the machine direction and in the cross-machine direction.

In a further alternative embodiment, an ultrasound velocity gauge 10″, as shown in FIG. 9, comprises four wheels mounted in a generally square configuration. A first wheel 14a″ transmits a signal which is picked up by a second wheel 14b″ in the cross machine direction and which is also picked up by a third wheel 14c″ in the machine direction. Such a velocity gauge 10″ can measure the velocity in the web 12 both in the cross machine direction and in the machine direction simultaneously. The fourth wheel 14d″, disposed diagonally to the first wheel 14a″, is generally a dummy wheel provided for symmetry so that the web 12 is held evenly on both sides. A receiving transducer may be located in the fourth wheel 14d″ to provide additional information e.g. estimate Poisson ratios.

While the present invention has been described in terms of certain preferred embodiments, modifications which are obvious to one skilled in the art may be made without departing from the teachings of the invention which are limited only by the following claims:

What is claimed is:

1. A device for measuring ultrasound velocities through a moving web comprising:
    a first rotating wheel having a peripheral surface for continuous surface contact with a moving web;
    an ultrasound transmitting means for converting an electrical signal to ultrasonic waves which propagate through the web and located in said first wheel in position to contact the web;
    a firing means for sending an electrical signal to said transmitting means when said transmitting means contacts the web;
    a second rotating wheel spaced apart from said first wheel having a peripheral surface for continuous surface contact with the web;
    a receiving means for converting ultrasonic waves to an electrical signal and located in said second wheel to contact the web on each revolution to receive ultrasonic waves from said transmitting means and produce therefrom an electrical signal;
    filtering means receiving said electrical signal;
    amplifying means receiving the filtered electrical signal and disposed in said second wheel;
    and a time metering means to measure the time of travel of the ultrasonic waves between said first wheel and said second wheel.

2. A device according to claim 1 wherein said wheels are shock mounted.

3. A device according to claim 1 wherein said wheels are spaced apart on a line generally orthogonal to the direction of movement of the web.

4. A device according to claim 1 wherein said wheels are spaced apart on a line generally parallel to the direction of movement of the web.

5. A device according to claim 1 also including a third wheel with a second receiving means therein to contact the web on each revolution at a time appropriate to receive ultrasonic waves from said transmitter, a second amplifying means located in said third wheel to enhance the electrical signal produced by said second receiving means, and a second time metering means to measure the traveling time of the ultrasonic waves between said first wheel and said third wheel, said second wheel spaced from said first wheel on a line orthogonal to the direction of movement of the web to measure the velocity of ultrasound waves in the cross machine direction and said third wheel spaced from said first wheel on a line parallel to the direction of the web to measure the velocity of ultrasound waves in the machine direction.

6. A device according to claim 1 also including a second amplifying means exterior to said second wheel to further enhance the electrical signal therefrom.

7. A device according to claim 1 also including a computing means for adjusting for time delays of the ultrasound signal in said wheels.

8. A device according to claim 7 wherein said computing means also averages the ultrasound transit time for a plurality of revolutions.

9. A device according to claim 1 wherein an output is produced which is compatible with a digital readout display.

10. A device according to claim 1 wherein an analog output is produced compatible with chart recorders.

11. A device according to claim 1 wherein a position detector is provided to activate said firing means when said transmitting means is on said web.

12. A device according to claim 1 wherein a strip with light reflective properties different than the light reflective properties of the surface of said wheels is located on a surface of one of said wheels, and said position detector optically detects said strip on each revolution of said wheels and activate said firing means.

13. A device according to claim 1 wherein a syncronizing means coordinates the rotation of said first wheel and said second wheel.

14. A device according to claim 13 wherein said syncronizing means comprises a timing rod and a chain linking each of said wheels to said timing rod.

15. A device according to claim 4 wherein a chain connects said first wheel to said second wheel to syncronize the rotation of said first and said second wheel.

16. A transducer for use in measuring ultrasonic velocities through a moving web comprising:
    a button for contact with the web to pass mechanical signals therebetween,
    first and second piezoelectric crystal with an electrode sandwiched therebetween, said first crystal in surface contact with said button to pass mechanical vibrations therebetween,
    said crystals oscillating in phase for the interconversion of electrical signals carried by said electrode and mechanical signals of said button, and
    standoff means to locate said button and said crystals above a base and absorb mechanical signals from said base.

17. A transducer according to claim 16 wherein said button is aluminum.

18. A transducer according to claim 16 wherein said standoff means are made of polymerized tetrafluoro ethylene.

19. A transducer according to claim 16 wherein a ballast is provided on a surface of said second crystal distal from said button to reduce surface reflection in said second crystal.

20. A transducer according to claim 19 wherein said ballast is aluminum.

21. A transducer according to claim 16 wherein said crystals are lead zirconate titanate.

* * * * *